US007923588B2

(12) United States Patent
Stephan et al.

(10) Patent No.: US 7,923,588 B2
(45) Date of Patent: Apr. 12, 2011

(54) PROCESS FOR PREPARING A C4-OLEFIN MIXTURE BY SELECTIVE HYDROGENATION AND METATHESIS PROCESS FOR USING THIS STREAM

(75) Inventors: Jürgen Stephan, Mannheim (DE); Andreas Brodhagen, Bierbeeg (BE); Markus Schubert, Ludwigshafen (DE); Frank Poplow, Ludwigshafen (DE); Michael Röper, Wachenheim (DE); Thomas Hill, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 733 days.

(21) Appl. No.: 11/665,161

(22) PCT Filed: Oct. 13, 2005

(86) PCT No.: PCT/EP2005/011027
§ 371 (c)(1),
(2), (4) Date: Dec. 17, 2007

(87) PCT Pub. No.: WO2006/040160
PCT Pub. Date: Apr. 20, 2006

(65) Prior Publication Data
US 2008/0188696 A1 Aug. 7, 2008

(30) Foreign Application Priority Data
Oct. 13, 2004 (DE) .................. 10 2004 049 940

(51) Int. Cl.
*C07C 7/167* (2006.01)
*C07C 11/08* (2006.01)
(52) U.S. Cl. .............. 585/16; 585/1; 585/643; 585/646; 585/258; 585/259; 585/260
(58) Field of Classification Search .......... None
See application file for complete search history.

(56) References Cited

U.S. PATENT DOCUMENTS

| 5,877,365 | A | 3/1999 | Chodorge et al. |
| 6,207,115 | B1 | 3/2001 | Chodorge et al. |
| 6,580,009 | B2 * | 6/2003 | Schwab et al. ............... 585/324 |
| 7,208,646 | B2 * | 4/2007 | Boyer ............... 585/259 |
| 7,226,527 | B2 * | 6/2007 | Bohner et al. ............... 203/2 |
| 2003/0136342 | A1 | 7/2003 | Mendez-Gallon et al. |
| 2004/0010161 | A1 | 1/2004 | Maas et al. |
| 2005/0107628 | A1 | 5/2005 | Roper et al. |

FOREIGN PATENT DOCUMENTS

| DE | 100 13 253 | 9/2001 |
| DE | 100 39 995 | 2/2002 |
| EP | 0 742 234 | 11/1996 |
| WO | 03 070669 | 8/2003 |

OTHER PUBLICATIONS

D. Commereuc et al., "Methathesis of ethylene-butene mixtures to propylene with rhenium on alumina catalysts," Journal of Molecular Catalysis, 65, 1991, pp. 39-50.
Johannes C. Mol, "Olefin metathesis over supported rehenium oxide catalysts," Catalysis Today, 51, (1999), pp. 289-299.
J.C. Mol et al., "Deactivation of rhenium-based catalysts for the metathesis of propene," Journal of Molecular Catalysis, 65, 1991, pp. 219-235.
J.A.K. du Plessis et al., "Re2O7/SiO2 Al2O3/SnMe4/1-octene catalytic system Part II. The influence of oxygen containing saturated hydrocarbons on the metathesis activity", Journal of Molecular Catalysis A: Chemical, 133, (1998), pp. 181-186.
Translation of International Preliminary Report on Patentability (Chapter II), for International Application No. PCT/EP2005/011027, 2005.

* cited by examiner

*Primary Examiner* — Tam M Nguyen
(74) *Attorney, Agent, or Firm* — Connolly Bove Lodge & Hutz LLP (57) ABSTRACT

A C4-olefin mixture having a 1,3-butadiene content of from 100 to 500 ppm and a content of 1,2-dienes of less than 10 ppm is described. The present invention further provides a process for preparing this C4-olefin mixture and provides for its use in a metathesis reaction for preparing 2-pentene and/or 3-hexene.

4 Claims, 4 Drawing Sheets

PROCESS FOR PREPARING A C4-OLEFIN MIXTURE BY SELECTIVE HYDROGENATION AND METATHESIS PROCESS FOR USING THIS STREAM

CROSS REFERENCE TO RELATED APPLICATIONS

This application is a National Stage entry under 35 USC §371 of PCT/EP2005/011027 filed on Oct. 13, 2005, which claims priority to German Application No. 10 2004 049 940.3 filed on Oct. 13, 2004. The entire contents of each of the above applications are incorporated herein by reference.

DESCRIPTION

The present invention relates to C4-olefin mixtures and a process for preparing them. In addition, the present invention relates to a process for preparing an olefin mixture comprising 2-pentene and/or 3-hexene by metathesis of the C4-olefin mixture over a metathesis catalyst.

Olefin metathesis has in recent years become an extremely valuable tool in organic synthesis. On an industrial scale too, a series of applications have become established, for example the Phillips process for preparing propene by ethenolysis (metathetic cleavage by means of ethene) of 2-butene or the process of Shell AG (SHOP) for preparing intern olefins in which the metathesis step is an important component.

A more recent example is the preparation of α,ω-dienes by ethenolysis of cycloolefins (FEAST process of Shell AG).

However, there is an important point which stands in the way of the valuable wide applicability of the metathesis reaction and which has long had a strong influence on the development of industrial processes: compared to other catalyst systems employed in industry, metathesis catalysts deactivate relatively quickly. Owing to the often expensive metathesis-active transition metal catalysts used, it is desirable to reduce or avoid deactivation, which is attributable, for example, to impurities in the feed.

The cause of the deactivation of metathesis catalysts has been intensively discussed in the literature. Examples are J. Mol. Cat. 1991, 65, pages 39-50 (Commereuc et al.), Catalysis today 1999, 51, pages 289-299 (J. C. Mol) and J. Mol. Cat. 1991, 65, pages 219-235 (J. C. Mol).

In principle, two deactivation routes have been postulated in the literature, namely an intrinsic route which is always present and also a deactivation mechanism which is caused by particular impurities in the feed stream. These impurities in the feed stream can have a reversible effect or act as permanent poisons.

In particular, isobutene and 1,3-butadiene are named as deactivating substances in the literature, since they tend to form oligomers by cationic mechanisms and these oligomers then function as diffusion barriers. Furthermore, polar, basic components have been named as an important class of deactivating substances. This influence is known and is avoided in the prior art by the use of adsorptive feed purification, viz. guard beds (e.g. molecular sieves). A detailed examination of the influence of oxygen-comprising compounds on metathesis catalysts may be found in J. A. K. du Plissis, J. Mol. Cat. A: Chemical, 1989, 133, pages 181-186. Zeolites or aluminum oxides, in particular, can be used for adsorptive feed purification.

The influence of acetylenic compounds and 1,3-dienes has likewise been described as important, cf. EP 742 234 A1. These components result in considerable deactivation which has to be countered in order to ensure economical operation of the reaction.

As a countermeasure against the 1,3-dienes and acetylenic compounds present in the C4 feed, a selective hydrogenation has been described, but this also isomerizes 1-butene to 2-butene. This measure therefore provides no help in achieving selective removal of 1,2-dienes with simultaneous retention of a high 1-butene content. However, the latter is necessary if the objective of the metathesis reaction is to produce large amounts of 3-hexene. WO 03/070669 A2 refers to the necessity of selective hydrogenation of the C4 fraction. Here, "low isom" conditions which lead to residual contents of from 0 to 50 ppm of 1,3-butadiene with very little isomerization of C—C double bonds are specified.

DE 100 13 253 A1 describes suitable pretreatments for C4 streams used for metathesis. Here, the removal of 1,3-butadiene and acetylenic compounds is achieved by extraction and/or selective hydrogenation. The limit for the sum of dienes is defined in DE 100 13 253 A1 as less than 10 ppm.

However, the pretreatments described in the abovementioned documents WO 03/070669 A2 and DE 100 13 253 A1 do not give streams which simultaneously have a low proportion of deactivating components and a high 1-butene content.

SUMMARY OF THE INVENTION

It is therefore an object of the present invention to provide a C4-olefin mixture which has a high 1-butene content and can be used in metathesis reactions without substantial deactivation of metathesis catalysts.

According to the invention, this object is achieved by a C4-olefin mixture which has a residual content of from 100 to 500 ppm of 1,3-butadiene but in which the content of the particularly strongly deactivating 1,2-dienes has been reduced to at least 10 ppm. According to the invention, it has been found that the deactivating effect of 1,2-dienes (e.g. propadiene or 1,2-butadiene) on metathesis catalysts significantly exceeds the effect of conjugated dienes (e.g. 1,3-butadiene) or alkynes (e.g. 1-butyne) and alkynenes (e.g. butenyne).

The present invention thus provides a C4-olefin mixture.

DESCRIPTION OF THE BEST AND VARIOUS EMBODIMENTS

The C4-olefin mixture of the invention has a 1,3-butadiene content of from 100 to 500 ppm, preferably from 110 to 400 ppm, particularly preferably from 120 to 300 ppm, and a content of cumulated dienes such as propadiene, 1,2-butadiene, 1,2-pentadiene or 2,3-pentadiene of less than 10 ppm, preferably from 1 to 10 ppm, particularly preferably from 2 to 10 ppm.

In a particular embodiment, the cumulated dienes are cumulated 1,2-dienes.

The ratio of 1-butene to 2-butene in the C4-olefin mixture is preferably from 1.2 to 2.0, particularly preferably from 1.3 to 1.6. The 1-butene content of the C4-olefin mixture, based on the mixture, is preferably at least 30% by weight, particularly preferably at least 40% by weight, in particular at least 50% by weight.

The C4-olefin mixture of the invention can comprise 1-butene, trans-2-butene, cis-2-butene, isobutene, isobutane und n-butane.

The C4-olefin mixture of the invention can be obtained by means of selective conditions of a hydrogenation which allow cumulated dienes to be removed to below 10 ppm and at the same time only little 1-butene to be isomerized, starting from outputs from steam crackers. A feed stream which is particularly advantageous for the metathesis of C4-olefin streams to mixtures comprising 2-pentene and/or 3-hexene is produced in this way.

The C4-olefin mixtures of the invention can thus be obtained by selective hydrogenation of outputs from steam crackers.

The present invention therefore also provides a process for preparing a C4-olefin mixture by hydrogenation of a C4-stream coming from steam crackers. The hydrogenation is preferably carried out in at least two hydrogenation stages.

In a preferred embodiment of the process of the invention, a C4 stream coming from a steam cracker is hydrogenated in at least two stages, with the first stage of the hydrogenation being carried out over a catalyst which comprises at least one metal of group VIII of the Periodic Table of the Elements as hydrogenation metal and, in addition, a promoter on an oxidic support, with at least 80% of the metal of group VIII of the Periodic Table of the Elements being distributed essentially homogeneously in a layer between the surface of the catalyst and a penetration depth corresponding to not more than 80% of the radius of the catalyst, calculated from the surface of the catalyst, and the promoter being distributed essentially homogeneously ever the entire cross section of the catalyst.

In a preferred embodiment, the catalyst has a diameter of from 2.5 to 10 mm, with at least 80% of the metal of group VIII of the Periodic Table of the Elements being distributed essentially homogeneously in a layer between the surface of the catalyst and a penetration depth of not more than 1000 µm, calculated from the surface of the catalyst, and the promoter being distributed essentially homogeneously over the entire cross section.

Thus, the invention provides for a catalyst in which the metal of group VIII of the Periodic Table of the Elements forms a shell structure in the catalyst while the promoter is completely permeated.

The designation of the groups of the Periodic Table of the Elements is in accordance with the CAS (chemical abstracts service) nomenclature.

The catalyst used according to the invention has a diameter of from 2.5 to 10 mm. In preferred embodiments of the catalyst according to the invention, the diameter is from 2.5 to 5 mm, in particular from 2.5 to 3.5 mm.

In the catalyst according to the invention, at least 80%, preferably at least 90%, particularly preferably at least 95%, in particular at least 98%, especially 100%, of the metal of group VIII of the Periodic Table of the Elements is distributed essentially homogeneously in a layer between the surface of the catalyst and a penetration depth of not more than 1000 µm, calculated from the surface of the catalyst.

The catalyst according to the invention comprises a metal of group VIII of the Periodic Table of the Elements (Fe, Ru, Os, Co, Rh, Ir, Ni, Pd, Pt). In a preferred embodiment of the present invention, the metal is palladium.

The catalyst according to the invention further comprises at least one promoter. This/these can be, for example, further metals of group VIII, group IB and group IIB of the Periodic Table of the Elements (Cu, Ag, Au, Zn, Cd, Hg). In a preferred embodiment, the catalysts according to the invention further comprise at least one metal of group IB of the Periodic Table of the Elements in addition to the metal of group VIII of the Periodic Table of the Elements. Particular preference is in this case given to silver.

In a particularly preferred embodiment, the catalyst according to the invention comprises palladium and silver.

The catalyst according to the invention can have any shapes, for example extrudates, hollow extrudates, pellets, rings, spherical particles or spheres. Preference is given to the catalyst according to the invention being in the form of an extrudate.

The metals can be present in pure metallic form, or else in the form of compounds, for example in the form of metal oxides. Under the operating conditions of a hydrogenation process, they are generally present in the form of metals. The conversion of any oxides into metals can be effected in a manner known to those skilled in the art before use of the catalyst in a hydrogenation process in or outside a hydrogenation reactor, for example by prereduction and, if necessary or advantageous for manipulations of the prereduced catalyst, subsequent surface passivation.

The content of the catalyst of metal or metals of group VIII of the Periodic Table, in particular palladium, is preferably at least 0.01% by weight, particularly preferably at least 0.1% by weight, in particular at least 0.15% by weight. This content is preferably not more than 5% by weight, particularly preferably not more than 1% by weight, in particular not more than 0.6% by weight. Although lower and higher contents are possible, they are normally economically unsatisfactory because of the activity being too low or raw material costs being too high. In a particularly preferred embodiment, only one hydrogenation metal, in particular palladium, is used.

The ratio of amounts of hydrogenation metal of group VIII of the Periodic Table of the Elements to additives or dopants is a parameter to be optimized in each individual case. The atomic ratio of metal of group VIII of the Periodic Table of the Elements, particularly preferably palladium, to the promoter, particularly preferably silver, is preferably 0.1-10, particularly preferably 2-7, in particular 2.5-6.

The oxidic support of the hydrogenation catalyst according to the invention is preferably aluminum oxide, particularly preferably in a mixture of δ-, θ- and α-aluminum oxide. The support can also comprise, apart from unavoidable impurities, amounts of other additives. For example, other inorganic oxides such as oxides of metals of groups IIA, IIB, IVB, IIIA and IVA of the Periodic Table of the Elements can also be present, in particular silicon dioxide, titanium dioxide, zirconium dioxide, zinc oxide, magnesium oxide, sodium oxide and calcium oxide. The maximum content of such oxides other than aluminum oxide in the support is dependent on the oxide actually present, but is to be determined in an individual case with the aid of the X-ray diffraction pattern of the hydrogenation catalyst, since any change in the structure is associated with a significant change in the X-ray diffraction pattern. In general, the content of such oxides other than aluminum oxide is below 50% by weight, preferably below 30% by weight, particularly preferably below 10% by weight. The purity of the aluminum oxide is preferably greater than 99%.

To prepare the support, a suitable aluminum-comprising raw material, preferably boehmite, is peptized by means of a peptizing agent such as water, dilute acid or dilute base. As acid, use is made, for example, of a mineral acid such as nitric acid, or an organic acid such as formic acid. As base, preference is given to using an inorganic base such as ammonia. The acid or base is generally dissolved in water. Preference is given to using water or dilute aqueous nitric acid as peptizing agent. The concentration of the nonaqueous component of the peptizing agent is generally 0-10% by weight, preferably 0-7% by weight, particularly preferably 0-5% by weight. Subsequent to the peptization, the support is shaped, dried and calcined.

Boehmite ($\gamma$-AlO(OH)) is a widely available commercial product, but can also be prepared in a known manner immediately before the actual preparation of the support by precipitation from a solution of an aluminum salt, for example aluminum nitrate, by means of a base, isolation, washing, drying and calcination of the precipitated solid. Boehmite is advantageously used in the form of a powder. A suitable commercial boehmite powder is, for example, Versal® 250, which is obtainable from UOP. The boehmite is treated with the peptizing agent by moistening it with the peptizing agent and mixing intensively, for example in a kneader, mixer or pan mill. Peptization is continued until the mass is readily shapeable. The mass is subsequently shaped by means of customary methods to give the desired shaped support bodies, for example by ram extrusion, screw extrusion, tabletting or agglomeration. Any known method is suitable for shaping. If necessary or advantageous, customary additives can be used. Examples of such additives are extrusion or tabletting aids, e.g. polyglycols or graphite.

It is also possible for additives which influence the pore structure of the support after calcination in a known manner as burn-out materials, for example polymers, fibrous materials, natural burn-out materials, e.g. ground nut shells, or other customary additives to be mixed into the raw support composition prior to shaping. Preference is given to the use of boehmite in a particle size distribution and the addition of burn-out materials which lead to a pore radius distribution of the finished support in which 50-90% by volume of the total pore volume is in the form of pores having a mean diameter in the range 0.01-0.1 µm and 10-50% by volume of the total pore volume being in the form of pores having a mean diameter in the range 0.1-1 µm. The measures necessary for this are known per se to those skilled in the art.

Subsequent to shaping, the shaped bodies are dried in a customary manner, in general at a temperature above 60° C., preferably above 80° C., particularly preferably above 100° C., in particular at a temperature in the range 120-300° C. Drying is continued until water present in the shaped bodies has been essentially completely given off from the shaped bodies, which is generally the case after a few hours. Usual drying times are in the range from 1 to 30 hours and are dependent on the drying temperature set, with a higher temperature shortening the drying time. Drying can also be accelerated further by application of a reduced pressure.

Subsequent to drying, the shaped bodies are converted into the finished support by calcination. The calcination temperature is generally in the range 900-1150° C., preferably in the range 1000-1120° C., particularly preferably in the range 1050-1100° C. The calcination time is generally in the range from 0.5 to 5 hours, preferably from 1 to 4 hours, particularly preferably from 1.5 to 3 hours. Calcination is carried out in a customary furnace, for example in a rotary tube furnace, in a tunnel kiln, in a belt calciner or in a muffle furnace. Calcination can also follow drying directly without the shaped bodies being cooled in between.

The catalysts according to the invention which are obtained in this way have a specific surface area (BET, Brunauer-Emmet-Teller, determined in accordance with DIN 66131 by nitrogen adsorption at 77 K) of 20-250 $m^2/g$, preferably 50-150 $m^2/g$, in particular 60-90 $m^2/g$. The surface area can be varied by known methods, in particular use of finely divided or relatively coarse starting materials, calcination time and calcination temperature. Like the BET surface area, the pore volume can also be varied in a known manner, and is generally, as determined by means of mercury porosimetry, in the range 0.3-1.0 ml/g, preferably in the range 0.4-0.9 ml/g, particularly preferably 0.5-0.8 ml/g.

After the calcination, the active composition and, if desired, further additives are deposited on the support prepared in this way.

The support of the catalyst according to the invention preferably displays the following X-ray diffraction pattern:

| Lattice plane spacing Angstrom [Å] | Angle 2-Theta [°] | Intensity [%] |
|---|---|---|
| d = 4.552 | 19.483 | 5-15 |
| d = 2.857 | 31.278 | 35-50 |
| d = 2.730 | 32.775 | 65-80 |
| d = 2.449 | 36.671 | 45-55 |
| d = 2.317 | 38.842 | 35-45 |
| d = 2.260 | 39.861 | 35-45 |
| d = 2.022 | 44.790 | 45-65 |
| d = 1.910 | 47.570 | 30-40 |
| d = 1.798 | 50.720 | 10-25 |
| d = 1.543 | 59.915 | 25-35 |
| d = 1.511 | 61.307 | 0-35 |
| d = 1.489 | 62.289 | 20-30 |
| d = 1.455 | 63.926 | 25-35 |
| d = 1.387 | 67.446 | 100 |

This X-ray diffraction pattern is determined as described in EP 0 992 284 A2 on page 9, lines 6 to 9.

X-ray diffraction patterns are characteristic of the specific structure of the material examined. The structure of the catalyst according to the invention is sufficiently well defined by the occurrence of the abovementioned reflections. In addition to the characteristic reflections indicated above, one or more reflections for the lattice plane spacings 3.48; 2.55; 2.38; 2.09; 1.78; 1.74; 1.62; 1.60; 1.57; 1.42; 1.40 and/or 1.37, all in the unit [Å], can occur in any intensity in the X-ray diffraction pattern.

Furthermore, any further reflections can additionally occur in the X-ray diffraction pattern of the catalyst according to the invention.

The active composition and, if appropriate, further additives can be deposited on the resulting support of the catalyst according to the invention.

The metals, additives and/or dopants to be deposited on the support can be applied to the support by any known method, for example by coating from the gas phase (chemical or physical vapor deposition) or steeping of the support material in a solution comprising the substances and/or compounds to be deposited.

The preferred method is impregnation with a solution of the substances and/or compounds to be deposited, which are converted during the course of the further preparation of the catalyst into the substances to be deposited. The substances to be deposited can be deposited individually and/or in partial amounts in a plurality of process steps or together and completely in one process step. Preference is given to joint deposition in one impregnation stage. Subsequent to impregnation or the individual impregnation stages, the supported catalyst is dried and converted by calcination and, if appropriate, other known after-treatment methods, for example activation and subsequent surface passivation, into the ready-to-use catalyst.

Impregnation methods for depositing active components, additives and/or dopants on a support are known. In general, the support is impregnated with a solution of salts of the components to be deposited, with the volume of the solution being selected so that the solution is virtually completely taken up by the pore volume of the support ("incipient wetness" method). The concentration of the salts in the solution is measured so that the components to be deposited are present on the catalyst in the desired concentrations after impregnation and conversion of the supported catalyst into the finished catalyst. The salts are chosen so that they leave behind no interfering residues in the preparation of the catalyst or its later use. Nitrates or ammonium salts are usually used.

All impregnation processes known to those skilled in the art are in principle suitable for preparing the catalyst according to the invention.

However, the catalyst according to the invention is preferably prepared using single-stage impregnation of the support with a nitric acid solution of the nitrates of the metals to be deposited by the incipient wetness method.

In a particularly preferred embodiment, an impregnation solution comprising both palladium nitrate and palladium nitrite is used.

In addition, the metal of group IB of the Periodic Table of the Elements, preferably silver nitrate, is also present in the impregnation solution.

In general, the pH of the impregnation solution is not more than 5, preferably not more than 2, particularly preferably not more than 1, in particular not more than 0.5. The lower limit of the pH is generally 0.2, preferably 0.3, particularly preferably 0.5. A particularly preferred pH range is from 0.3 to 0.5.

After impregnation, the impregnated support is dried in a customary fashion, generally at a temperature above 60° C., preferably above 80° C., particularly preferably above 100° C., in particular at a temperature in the range 120-300° C. Drying is continued until water present in the impregnated catalyst has been essentially completely given off, which is generally the case after a few hours. Usual drying times are in the range 1-30 hours and are dependent on the drying temperature set, with a higher drying temperature shortening the drying time. Drying can be accelerated further by application of a reduced pressure.

In a particularly preferred embodiment of the process of the invention, drying of the impregnated catalyst is carried out with the impregnated support material being kept in motion at the same time, for example in a rotary tube furnace.

In a particular embodiment of the present invention, the stream of air used for drying is conveyed through the rotary tube in countercurrent.

Subsequent to drying, the catalyst is prepared in a customary manner by calcination. This calcination serves essentially to convert the impregnated salts which have been applied into the components to be deposited or precursors of such components and in this respect differs from the above-described calcination which serves to produce the support material and the support structure. In the case of impregnation with metal nitrates, the nitrates are essentially decomposed into metals and/or metal oxides which remain in the catalyst and nitrous gases which are given off in this calcination.

The calcination temperature is generally 200-900° C., preferably 280-800° C., particularly preferably 300-700° C. The calcination time is generally in the range from 0.5 to 20 hours, preferably from 0.5 to 10 hours, particularly preferably from 0.5 to 5 hours. Calcination is carried out in a customary furnace, for example in a rotary tube furnace, in a belt calciner or in a muffle furnace. Calcination can follow drying directly without the supported and dried catalyst being cooled in between.

In a particularly preferred embodiment of the process of the invention, drying and calcination of the catalyst are carried out together in a rotary tube furnace.

After the calcination, the catalyst is in principle ready to use. If necessary or desired, it is activated in a known manner by prereduction and, if appropriate, passivated again on its surface before installation in the hydrogenation reactor.

However, the reduction of the hydrogenation catalyst generally occurs in the hydrogenation reactor itself. This is effected in a manner known to those skilled in the art by firstly establishing inert conditions by means of nitrogen or another inert gas. The reduction is carried out using a hydrogen-comprising gas as pure gas phase or with circulation of inert gas. The temperature at which this prereduction is carried out is generally 5-200° C., preferably 20-150° C.

Regeneration of the catalyst according to the invention can also be carried out outside or within the hydrogenation reactor at temperatures of from 15 to 500'C.

The hydrogenation of the output from the steam cracker over the above-described catalyst is preferably carried out at a pressure of from 5 to 50 barg. The inlet temperature is preferably from 20 to 100° C., with the temperature increase preferably being from 10 to 60° C. The fresh feed throughput (whsv) is preferably from 0.5 to 15 kg/lh. The ratio of recycle stream to fresh feed is preferably from 2 to 20 and the superficial velocity is preferably from 20 to 400 m/h. The ratio of hydrogen to butadiene is preferably from 1 to 1.5.

This hydrogenation preferably gives a C4-olefin mixture having a 1,3-butadiene content of from 100 to 500 ppm, preferably from 110 to 400 ppm, particularly preferably from 120 to 300 ppm, and a content of cumulated dienes such as propadiene, 1,2-butadiene, 1,2-pentadiene or 2,3-pentadiene of less than 10 ppm, preferably from 1 to 10 ppm, particularly preferably from 2 to 10 ppm.

The 1-butene content of the hydrogenated C4 stream is preferably 30%, particularly preferably 40%, in particular 50% (after isobutene removal, residual isobutene: preferably from 0.5 to 4%, particularly preferably from 1 to 3%), while the ratio of 1-butene to 2-butene is preferably from 1.2 to 2.0, particularly preferably from 1.3 to 1.6.

In a particularly preferred embodiment, the process of the invention is carried out in a plurality of stages, particularly preferably in three stages.

In this embodiment, the first hydrogenation stage takes place over the above-described catalyst according to the invention in such a way that the stream to be hydrogenated from the steam cracker is reacted in an essentially liquid phase, which may also comprise hydrogen to the extent of its solubility, with an essentially gaseous hydrogen-comprising phase. As an alternative, the hydrogenation can also be carried out essentially in only a liquid phase, so that all of the hydrogen is present in solution in the liquid phase.

The inlet temperature is preferably from 20 to 100° C., particularly preferably from 30 to 90° C., in particular from 30 to 80° C. The hydrogenation occurs with a temperature increase of preferably from 10 to 60° C., particularly preferably from 20 to 50° C., in particular from 25 to 45° C.

The pressure during the first hydrogenation is preferably from 5 to 50 barg, particularly preferably from 5 to 30 barg, in particular from 10 to 30 barg.

The fresh feed throughput (whsv) in the first hydrogenation stage is preferably from 0.5 to 15 kg/lh, particularly preferably from 1 to 10 kg/lh, in particular from 1.5 to 8 kg/lh.

The first hydrogenation stage is preferably carried out so that the superficial velocity during the hydrogenation can preferably be from 20 to 400 in/h.

The ratio of hydrogen to butadiene in the first hydrogenation stage is preferably from 0.7 to 1.5, particularly preferably from 0.8 to 1.2, in particular from 19 to 1.0, with the butadiene content at the outlet preferably being from 0.05 to 10% by weight, particularly preferably from 2 to 6% by weight, in particular from 3 to 5% by weight.

The ratio of recycle stream to fresh feed is preferably from 2 to 20, particularly preferably from 2 to 15, in particular from 5 to 12.

In the first hydrogenation stage, the content of inert compounds in the hydrogen used for the hydrogenation can preferably be from 0 to 30% by volume, particularly preferably from 0 to 15% by volume.

The hydrogenation of the second process stage can in principle be carried out over any suitable catalyst.

The hydrogenation catalyst for the second hydrogenation stage can be, for example, a catalyst comprising at least one element of group VIII of the Periodic Table of the Elements, with one of these elements preferably being palladium. The content of this element in the catalyst, based on the catalyst, is preferably from 0.05 to 2% by weight, particularly preferably from 0.1 to 0.3% by weight.

The catalyst preferably comprises at least one promoter, more preferably an element of group IB of the Periodic Table of the Elements, in particular silver. The amount of promoter is preferably from 0.01 to 1% by weight, particularly preferably from 0.05 to 0.5% by weight.

Particular preference is given to the integral atomic ratio of palladium/silver in the catalyst being from 0.1 to 10, particularly preferably from 0.5 to 5.

The catalyst preferably comprises an oxidic support, with aluminum oxide ($Al_2O_3$) being preferred as support material. The BET surface area of the support material is preferably from 1 to 250 $m^2/g$, particularly preferably from 30 to 150 $m^2/g$, in particular from 60 to 90 $m^2/g$.

The hydrogenation in the second stage of the process is preferably carried out as follows:

The hydrogenation in the second process stage can be carried out using an essentially liquid C4-olefin mixed phase, which can also comprise hydrogen to the extent of its solubility, with an essentially gaseous hydrogen-comprising phase. As an alternative, the hydrogenation can also be carried out in essentially only a liquid phase, so that all of the hydrogen is present in solution in the liquid phase.

The pressure in the second process stage is preferably from 5 to 50 barg, particularly preferably from 5 to 30 barg, in particular from 10 to 30 barg.

The temperature on entry to the second hydrogenation stage is preferably from 20 to 100° C., particularly preferably from 30 to 90° C., in particular from 40 to 90° C. The hydrogenation is carried out with a temperature increase of preferably from 10 to 60° C., particularly preferably from 5 to 20° C., in particular from 5 to 15° C.

The fresh feed throughput (whsv) is preferably from 0.5 to 15 kg/lh, particularly preferably from 1 to 12 kg/lh, in particular from 2 to 10 kg/lh.

The hydrogenation can be carried out in the circulation mode or in a single pass. The ratio of recycle stream to fresh feed is preferably from 0 to 20, particularly preferably from 0 to 10, in particular from 0 to 7.

The superficial velocity in the second hydrogenation stage is preferably from 20 to 400 m/h.

The ratio of hydrogen to butadiene in the second hydrogenation stage is preferably from 1 to 3, particularly preferably from 1 to 2, in particular from 1 to 1.3.

If the process of the invention is carried out in at least three stages, the 1,3-butadiene content at the outlet from the second hydrogenation stage is preferably from 0.005 to 0.05%, by weight particularly preferably from 0.01 to 0.5% by weight, in particular from 0.1 to 0.2% by weight. The sum of cumulated dienes is then preferably from 0 to 100 ppm by weight, particularly preferably from 0 to 10 ppm by weight.

If the process of the invention is carried out in two stages, it gives a C4-olefin mixture having a 1,3-butadiene content of from 100 to 500 ppm, preferably from 110 to 400 ppm, particularly preferably from 120 to 300 ppm, and a content of cumulated dienes such as propadiene, 1,2-butadiene, 1,2-pentadiene or 2,3-pentadiene of less than 10 ppm, preferably from 1 to 10 ppm, particularly preferably from 2 to 10 ppm.

The reaction in the second hydrogenation stage is carried out, in a manner analogous to the first hydrogenation stage, under conditions known per se to those skilled in the art, e.g. adiabatically or with evaporative cooling.

The content of inert compounds in the hydrogen used in the second hydrogenation stage is preferably from 0 to 30% by volume, particularly preferably from 0 to 15% by volume.

The 1-butene content of the hydrogenated C4 mixture after i-butene removal is preferably 30%, particularly preferably 40%, in particular 50%, with the ratio of 1-butene to 2-butene preferably being from 1.2 to 2.0, particularly preferably from 1.3 to 1.6.

Furthermore, the process of the invention can comprise further hydrogenation stages or methods of determining the 1,2-diene content.

If the process of the invention comprises a third hydrogenation stage (fine hydrogenation), this hydrogenation stage is preferably carried out under the following conditions:

When a further, third hydrogenation stage is carried out in the process of the invention, this can be carried out using any suitable catalyst, including the catalyst used in the first hydrogenation stage.

The hydrogenation catalyst for this optional third hydrogenation stage can be, for example, a catalyst comprising at least one element of group VIII of the Periodic Table of the Elements, with one of these elements preferably being palladium. The content of this element in the catalyst, based on the catalyst, is preferably from 0.05 to 2% by weight, particularly preferably from 0.1 to 0.3% by weight.

The catalyst preferably comprises at least one promoter, preferably an element of group IB of the Periodic Table of the Elements, in particular silver. The amount of promoter is preferably from 0.01 to 1% by weight, particularly preferably from 0.05 to 0.5% by weight.

Particular preference is given to the integral atomic ratio of palladium/silver in the catalyst being from 0.1 to 10, particularly preferably from 0.5 to 5.

The catalyst preferably comprises an oxidic support, with aluminum oxide ($Al_2O_3$) being preferred as support material. The BET surface area of the support material is preferably from 1 to 250 $m^2/g$, particularly preferably from 30 to 150 $m^2/g$, in particular from 60 to 90 $m^2/g$.

The hydrogenation in the third process stage can be carried out using an essentially liquid C4-olefin mixed phase, which can also comprise hydrogen to the extent of its solubility, with an essentially gaseous hydrogen-comprising phase. As an alternative, the hydrogenation can also be carried out in essentially only a liquid phase, so that all of the hydrogen is present in solution in the liquid phase.

The pressure is preferably from 5 to 30 barg, particularly preferably from 10 to 30 barg.

The temperature on entry into the hydrogenation of the third process stage is preferably from 30 to 90° C., particularly preferably from 40 to 85° C. A temperature increase of preferably from 0 to 20° C., particularly preferably from 0 to 10° C., is set.

The fresh feed throughput (whsv) is preferably from 1 to 12 kg/lh, particularly preferably from 3 to 10 kg/lh.

The ratio of hydrogen to butadiene is preferably from 1 to 10, particularly preferably from 1 to 8.

The content of inert compounds in the hydrogen used for the hydrogenation can be from 0 to 30% by volume, in particular from 0 to 15% by volume.

The 1-butene content of the hydrogenated C4 stream is preferably 30%, particularly preferably 40%, in particular 50% (after isobutene removal, residual isobutene: preferably from 0.5 to 4%, particularly preferably from 1 to 3%), while the ratio of 1-butene to 2-butene is preferably from 1.2 to 2.0, particularly preferably from 1.3 to 1.6.

The reaction can be carried out in a customary way as is known to those skilled in the art, for example adiabatically or with evaporative cooling.

The butadiene content at the outlet from this third hydrogenation stage is preferably from 0.07 to 0.05% by weight, particularly preferably from 0.01 to 0.02% by weight.

The sum of dienes remaining in the stream after the third hydrogenation stage is preferably from 0 to 10 ppm by weight.

In a preferred embodiment of the present invention, the process of the invention is suitable for preparing the C4-olefin stream of the invention having a 1,3-butadiene content of from 100 to 500 ppm, preferably from 110 to 400 ppm. Particular preference is given to from 120 to 300 ppm, and a content of cumulated 1,2-dienes such as propadiene, 1,2-butadiene, 1,2-pentadiene or 2,3-pentadiene of less than 10 ppm, preferably from 1 to 10 ppm, particularly preferably from 2 to 10 ppm.

The present invention further provides the C4-olefin mixtures obtainable by the selective hydrogenation process described above.

The present invention further provides a process for preparing an olefin mixture comprising 2-pentene and/or 3-hexene by reaction of the above-described $C_4$-olefin mixture over a metathesis catalyst. For the purposes of the present invention, the term "olefin mixture comprising 2-pentene and/or 3-hexene" refers to mixtures comprising 2-pentene and/or 3-hexene and also pure 2-pentene and pure 3-hexene.

The metathesis can, for example, be carried out as described in WO 00/39058 or DE-A-100 13 253.

Olefin metathesis (disproportionation) in its simplest form describes the reversible, metal-catalyzed transalkylidenation of olefins by rupture or reformation of C=C double bonds according to the following equation:

In the specific case of the metathesis of acyclic olefins, a distinction is made between self-metathesis in which an olefin is converted into a mixture of two olefins having different molar masses (for example: propene→ethene+2-butene) and cross-metathesis or cometathesis, which describes a reaction of two different olefins (propene+1-butene→ethene+2-pentene). If one of the reactants is ethene, the reaction is generally referred to as an ethenolysis.

Suitable metathesis catalysts are in principle homogeneous and heterogeneous transition metal compounds, in particular those of transition groups VI to VIII of the Periodic Table of the Elements, and also homogeneous and heterogeneous catalyst systems in which these compounds are present.

For the purposes of the present invention, it is generally possible to use all metathesis processes which start out from $C_4$ streams.

Thus, DE 199 32 060 A1 describes a process for preparing $C_5$-/$C_6$-olefins by reaction of a starting stream comprising 1-butene, 2-butene and isobutene to give a mixture of $C_{2-6}$-olefins. Here, propene, in particular, is obtained from butenes. In addition, hexene and methylpentene are discharged as products. No ethene is introduced into the metathesis. If appropriate, ethene formed in the metathesis is recirculated to the reactor.

However, the metathesis process which is preferred according to the present invention is the preparation of streams comprising 2-pentene and/or 3-hexene from the above-described raffinate II starting stream which has been treated according to the invention and comprises olefinic $C_4$-hydrocarbons. In a first embodiment, this process comprises a) carrying out a metathesis reaction in the presence of a metathesis catalyst comprising at least one compound of a metal of transition group VIIb, VIIb or VIII of the Periodic Table of the Elements, in which reaction butenes present in the starting stream are reacted with ethene to form a mixture comprising ethene, propene, butenes, 2-pentene, 3-hexene and butanes, with up to 0.6 molar equivalents of ethene, based on the butenes, being able to be used, b) firstly separating the resulting output stream into possibly a low-boiling fraction A comprising $C_2$-$C_3$-olefins and a high-boiling fraction comprising $C_4$-$C_6$-olefins and butanes by distillation, c) subsequently separating any low-boiling fraction A obtained from b) into an ethene-comprising fraction and a propene-comprising fraction by distillation, with the ethene-comprising fraction being recirculated to process step a) and the propene-comprising fraction being discharged as product, d) subsequently separating the high-boiling fraction obtained from b) into a low-boiling fraction B comprising butenes and butanes, an intermediate-boiling fraction C comprising 2-pentene and a high-boiling fraction D comprising 3-hexene by distillation, e) the fractions B and, if appropriate, C being wholly or partly recirculated to process step a) and the fraction D and, if appropriate, C being discharged as product.

A second embodiment comprises the following process steps:

a) carrying out a metathesis reaction in the presence of a metathesis catalyst comprising at least one compound of a metal of transition group VIIb, VIIb or VIII of the Periodic Table of the Elements, in which reaction butenes present in the starting stream are reacted with ethene to give a mixture comprising ethene, propene, butenes, 2-pentene, 3-hexene and butanes, with up to 0.6 molar equivalents based on the butenes of ethene, being able to be used, b) firstly separating the resulting starting stream by distillation into a low-boiling $C_2$ fraction which is removed via the top of a distillation column, a low-boiling $C_3$ fraction which is subsequently likewise removed via the top of the distillation column, to give a high-boiling fraction comprising C$_4$-C$_6$-olefins and butanes;

c) recirculating the low-boiling C2 fraction obtained in process step (2) to process step (1) and discharging the low-boiling C3 fraction as product;

d) subsequently separating the high-boiling fraction obtained from b) into a low-boiling fraction B comprising butenes and butanes, an intermediate-boiling fraction C comprising 2-pentene and a high-boiling fraction D comprising 3-hexene by distillation, e) the fractions B and, if appropriate, C being wholly or partly recirculated to process step a) and the fraction D and, if appropriate, C being discharged as product.

The difference between the second embodiment and the first embodiment is thus that the second embodiment provides, instead of the process steps b) and c), for a C2 fraction (low-boiling fraction A1) firstly to be separated off from the starting stream obtained in process step a) via the top of a distillation column and for a C3 fraction (low-boiling fraction A2) subsequently to be separated off via the top of the distillation column to give a high-boiling fraction comprising C$_4$-C$_6$-olefines and butanes and then processing the latter further in process step d).

The individual streams and fractions can comprise the specified compounds or consist of them. If they consist of the streams or compounds, the presence of relatively small amounts of other hydrocarbons is not ruled out.

In a single-stage reaction, the fraction according to the invention comprising C$_4$-olefins, preferably n-butenes and butanes, is reacted, if appropriate, with variable amounts of ethene in a metathesis reaction over a homogeneous or preferably heterogeneous metathesis catalyst to give a product mixture comprising (inert) butanes, unreacted 1-butene, 2-butene and the metathesis products ethene, propene, 2-pentene and 3-hexene. The desired products 2-pentene and/or 3-hexene are discharged, and the remaining products and unreacted compounds are wholly or partly recirculated to the metathesis. They are preferably recirculated essentially in their entirety, with only small amounts being discharged to avoid accumulation. Ideally, no accumulation occurs and all compounds apart from 3-hexene are recirculated to the metathesis.

According to the invention, use is made of up to 0.6, preferably up to 0.5, molar equivalents of ethene, based on the butenes, in the C$_4$ feed stream according to the invention. Thus, only small amounts of ethene, compared to the prior art, are used.

If no additional ethene is introduced, only up to a maximum of about 1.5%, based on the reaction products, of ethene is formed in the process, and this is recirculated, cf. DE 199 32 060 A 1. According to the invention, it is also possible to use larger amounts of ethene, with the amounts used being significantly smaller than in the known processes for preparing propene.

In addition, the maximum possible amounts of C$_4$ products and any C$_5$ products present in the reactor output are recirculated according to the invention. This applies, in particular, to the recirculation of unreacted 1-butene and 2-butene and any 2-pentene formed.

If small amounts of isobutene are still present in the C$_4$ feed stream, small amounts of branched hydrocarbons can also be formed.

The amount of branched C$_5$- and C$_6$-hydrocarbons which may additionally be formed in the output from the metathesis is dependent on the isobutene content of the C$_4$ feed and is preferably kept very low (<3%).

To illustrate the process of the invention in a plurality of variants, the reaction taking place in the metathesis reactor will be divided into three important individual reactions:

1. Cross-metathesis of 1-butene with 2-butene

2. Self-metathesis of 1-butene

3. Possibly ethenolysis of 2-butene

Depending on the respective demand for the target products propene and 3-hexene (for the purposes of the present invention, the term 3-hexene includes, inter alia, any isomers formed) or 2-pentene, the external mass balance of the process can be influenced in a targeted manner by varying the use of ethene and by shifting the equilibrium by recirculating particular substreams. Thus, for example, the 3-hexene yield can be increased by suppressing the cross-metathesis of 1-butene with 2-butene by recirculation of 2-pentene to the metathesis step, so that no or very little 1-butene is consumed here. In the self-metathesis of 1-butene to 3-hexene which then proceeds preferentially, additional ethene is formed and this reacts with 2-butene in a subsequent reaction to form the desired product propene.

The butene content of the C$_4$ fraction according to the invention used in the process is from 1 to 100% by weight, preferably from 60 to 90% by weight. The butene content is made up of 1-butene, 2-butene and isobutene.

The above-described C$_4$-olefin mixture used according to the invention can, if appropriate, be treated in an appropriate treatment over adsorber guard beds, preferably over high-surface-area aluminum oxides or molecular sieves, to free it of interfering impurities prior to the metathesis reaction.

The low-boiling fraction A comprising C$_2$-C$_3$-olefins which may be obtained from step b) is seperated into an ethene-comprising fraction and a propene-comprising fraction by distillation. The ethene-comprising fraction is then recirculated to process step a), i.e. the metathesis, and the propene-comprising fraction is discharged as product.

In step d), the separation into low-boiling fraction B, intermediate-boiling fraction C and high-boiling fraction D can, for example, be carried out in a dividing wall column. Here, the low-boiling fraction B is obtained at the top, the intermediate-boiling fraction C is obtained via a middle offtake and the high-boiling fraction D is obtained at the bottom.

However, to enable the varying amounts of products obtained in the flexibly controlled process to be handled better, it is advantageous to carry out a two-stage fractionation of the high-boiling fraction obtained from b). Preference is given to firstly separating the high-boiling fraction obtained from b) into a low-boiling fraction B comprising butenes and butanes and a high-boiling fraction comprising 2-pentene and 3-hexene by distillation. The high-boiling fraction is then separated into the fractions C and D by distillation.

The metathesis reaction is preferably carried out in the presence of heterogeneous metathesis catalysts which have no or only little isomerization activity and are selected from the class of transition metal compounds of metals of group VI.b, VII.b or VIII of the Periodic Table of the Elements applied to inorganic supports.

Preference is given to using rhenium oxide on a support, preferably on γ-aluminum oxide or on $Al_2O_3/B_2O_3/SiO_2$ mixed supports, as metathesis catalyst.

In particular, $Re_2O_7/\gamma\text{-}Al_2O_3$ having a rhenium oxide content of from 1 to 20% by weight, preferably from 3 to 15% by weight, particularly preferably from 6 to 12% by weight, is used as catalyst.

The metathesis is, in the liquid-phase mode, preferably carried out at a temperature of from 0 to 150° C., particularly preferably from 20 to 80° C., and a pressure of from 2 to 200 bar, particularly preferably from 5 to 30 bar.

If the metathesis is carried out in the gas phase, the temperature is preferably from 20 to 300° C., particularly preferably from 50 to 200° C. The pressure is in this case preferably from 1 to 20 bar, particularly preferably from 1 to 5 bar.

The present invention further provides the preparation of $C_5/C_6$-olefins using the substeps (1) to (4):
(1) Removal of butadiene and acetylenic compounds by, if appropriate, extraction of butadiene with a butadiene-selective solvent and subsequent selective hydrogenation according to the invention of the remaining butadienes and acetylenic impurities present to give a reaction output comprising n-butenes and isobutene and essentially no butadienes and acetylenic compounds,
(2) removal of isobutene by reaction of the reaction output obtained in the previous stage with an alcohol in the presence of an acid catalyst to form an ether, removal of the ether and the alcohol, which can be effected simultaneously or after the etherification, to give a reaction output comprising n-butenes and possibly oxygen-comprising impurities, with ether formed being able to be discharged or redissociated to recover isobutene and a distillation step for the removal of isobutene being able to follow the etherification step, with any $C_3$-, i-$C_4$- and $C_5$-hydrocarbons introduced being able to be removed by distillation during the work-up of the ether, or oligomerization or polymerization of isobutene from the reaction output obtained in the previous stage in the presence of an acid catalyst whose acid strength is suitable for the selected removal of isobutene from oligoisobutene or polyisobutene to give a stream having a residual isobutene content of from 0 to 15%,
(3) removal of the oxygen-comprising impurities from the output from the previous steps over appropriately selected adsorber materials,
(4) metathesis reaction of the resulting raffinate II stream as described.

The selective hydrogenation is carried out as described above.

The precise way in which the metathesis stage is carried out is preferably as follows:

The raffinate II stream obtained after etherification/polymerisation (or distillation) is preferably purified over at least one guard bed comprising high-surface-area aluminum oxides, silica gels, aluminosilicates or molecular sieves. The guard bed serves to dry the $C_4$ stream and to remove substances which can act as catalyst poisons in the subsequent metathesis step. Preferred adsorber materials are Selexsorb CD and CDO and also 3 Å and NaX molecular sieves (13×). Purification is carried out in drying towers at temperatures and pressures which are selected so that all components are present in the liquid phase. If appropriate, the purification step is used for preheating the feed for the subsequent metathesis step.

The remaining raffinate II stream is largely free of water, oxygen-comprising compounds, organic chlorides and sulfur compounds. The procedure is generally applicable to $C_4$ starting streams.

When the etherification step is carried out using methanol so as to prepare MTBE, it may be necessary, owing to the formation of dimethyl ether as secondary component, to combine a plurality of purification steps or to carry them out sequentially.

As metathesis catalysts, preference is given to heterogeneous rhenium catalysts such as $Re_2O_7$ on γ-$Al_2O_3$ or on mixed supports, e.g. $SiO_2/Al_2O_3$, $B_2O_3/SiO_2/Al_2O_3$ or $Fe_2O_3/Al_2O_3$, having varying metal contents known from the literature. The rhenium oxide content is, depending on the support selected, in the range from 1 to 20%, preferably from 3 to 10%.

The catalysts are generally used in freshly calcined form and require no further activation (e.g. by means of alkylating agents). Deactivated catalyst can be regenerated repeatedly by burning off carbon residues at temperatures above 400° C. in a stream of air and cooling under an inert gas atmosphere.

A comparison of the heterogeneous catalysts shows that $Re_2O_7/Al_2O_3$ is active even under very mild reaction conditions (T=20 to 80° C.), while $MO_3/SiO_2$ (M=Mo, W) becomes active only at temperatures above 100-150° C. and as a consequence C=C double bond isomerization can occur as secondary reactions.

Mention may also be made of
$WO_3/SiO_2$, prepared from $(C_5H_5)W(CO)_3Cl$ and $SiO_2$ in J. Mol. Catal. 1995, 95, 75-83;
3-component system comprising $[Mo(NO)_2(OR)_2]n$, $SnEt_4$ and $AlCl_3$ in J. Mol. Catal. 1991, 64, 171-178 and J. Mol. Catal. 1989, 57, 207-220;
nitridomolybdenum(VI) complexes from highly active precatalysts in J. Organomet. Chem. 1982, 229, $C_{19}$-$C_{23}$;
heterogeneous $SiO_2$-supported $MoO_3$ and $WO_3$ catalysts in J. Chem. Soc., Faraday Trans./1982, 78, 2583-2592;
supported Mo catalysts in J. Chem. Soc., Faraday Trans./1981, 77, 1763-1777;
active tungsten catalyst precursor in J. Am. Chem. Soc. 1980, 102(21), 6572-6574;
acetonitrile(pentacarbonyl)tungsten in J. Catal. 1975, 38, 482-484;
trichloro(nitrosyemolybdenum(II) as catalyst precursor in Z. Chem. 1974, 14, 284-285;
$W(CO)_5PPH_3/EtAlCl_2$ in J. Catal. 1974, 34, 196-202;
$WCl_6$/n-BuLi in J. Catal 1973, 28, 300-303;
$WCl_6$/n-BuLi in J. Catal. 1972, 26, 455-458;
FR 2 726 563: $O_3ReO[Al(OR)(L)xO]nReO_3$ where R=$C_1$-$C_{40}$-hydrocarbon, n=1-10, x=0 or 1 and L=solvent,
EP-A-191 0 675, EP-A-129 0 474, BE 899897: catalyst systems comprising tungsten, 2-substituted phenoxide radicals and 4 other ligands, including a halogen, alkyl or carbene group, FR 2 499 083: catalyst system comprising an oxo tungsten, molybdenum or rhenium complex with a Lewis acid.

U.S. Pat. No. 4,060,468: catalyst system comprising a tungsten salt, an oxygen-comprising aromatic compound, e.g. 2,6-dichlorophenol, and, if desired, molecular oxygen.

BE 776,564: catalyst system comprising a transition metal salt, an organometallic compound and an amine.

To improve the cycle duration of the catalysts used, especially the supported catalysts, the use of feed purification over guard beds is advisable. The guard bed serves to dry the $C_4$ stream and to remove substances which can act as catalyst poisons in the subsequent metathesis step. Preferred adsorber materials are Selexsorb CD and CDO and also 3 Å and NaX molecular sieves (13×). Purification is carried out in drying towers at temperatures and pressures which are preferably selected so that all components are present in the liquid phase. If appropriate, the purification step is used for preheating the feed for the subsequent metathesis step. It can be advantageous to combine a plurality of purification steps with one another or to carry them out sequentially.

Pressure and temperature in the metathesis step are selected so that all reactants are present in the liquid phase (usually from 0 to 150° C., preferably from 20 to 80° C.; p=2 to 200 bar). Alternatively, it can be advantageous, especially in the case of feed streams having a relatively high isobutene content, to carry out the reaction in the gas phase and/or to use a catalyst which has a relatively low acidity.

In general, the reaction is complete after from 1 s to 1 h, preferably after from 30 s to 30 min. It can be carried out continuously or batchwise in reactors such as pressurized gas vessels, flow tubes or reactive distillation apparatuses, with flow tubes being preferred.

The present invention further provides for the use of $C_4$-olefin mixtures for preparing 2-pentene and/or 3-hexene.

The present invention is illustrated by the following examples.

EXAMPLES

Procedure

A C4 stream from a steam cracker is subjected to a three-stage hydrogenation, with a hydrogenation over the catalyst provided according to the invention being carried out in the first hydrogenation stage.

The composition of the starting stream and the compositions obtained from the respective stages are shown in Table 1 below. The example demonstrates that it is possible to minimize the proportion of 1,2-dienes in the output from the steam cracker and also to maximize the 1-butene content, in this case to 50.70% by weight, by means of the hydrogenation over the catalyst according to the invention and by means of the process of the invention.

The respective process conditions are likewise shown in Table 1.

TABLE 1

|  |  | Starting material | 1st stage | 2nd stage | Raff2 | 3rd stage |
|---|---|---|---|---|---|---|
| 1,3-Butadiene | [% by weight] | 37.8 | 3.5 | 0.15 | 0.1992 | 0.0100 |
| 1-Butene | [% by weight] | 17.9 | 39.4 | 38.82 | 51.56 | 50.53 |
| trans-2-Butene | [% by weight] | 6.9 | 15.7 | 18.0 | 23.96 | 24.44 |
| cis-2-Butene | [% by weight] | 4.0 | 8.4 | 9.5 | 12.60 | 12.84 |
| i-Butene | [% by weight] | 26.7 | 26.7 | 26.7 | 2 | 2 |
| i-Butane | [% by weight] | 1.1 | 1.1 | 1.1 | 1.46 | 1.46 |
| n-Butane | [% by weight] | 5.0 | 5 | 5.5 | 7.30 | 7.80 |
| Butenyne | [% by weight] | 0.3 | <0.0002 | <0.0002 | <0.0002 | <0.0002 |
| Butyne | [% by weight] | 0.1 | <0.0002 | <0.0002 | <0.0002 | <0.0002 |
| 1,2-Butadiene | [ppm by weight] | 1900 | 70 | <2 | <2 | <2 |
| Propadiene | [ppm by weight] | 50 | <2 | <2 | <2 | <2 |
| Total 1,2-dienes | [ppm by weight] | 1950 | 70 | <4 |  | <4 |
| 1,3-Butadiene | [ppm by weight] |  |  |  |  | 100 |
| Overall butene sel. | [%] |  | 100.0 |  |  |  |
| 1-Butene sel. | [%] |  | 62.0 |  |  |  |
| Conversion | [%] |  | 90.74 | 95.71 |  | 94.98 |
| 1-B/2-B |  | 1.64 | 1.64 | 1.41 | 1.41 | 1.36 |
| 1-Butene obtained | [%] |  |  | 98.5 |  | 98 |
| n-Butane formation | [%] |  | 0 | 0.5 |  | 0.5 |
| Total butenes | [%] |  |  |  | 88.11 | 87.80 |
| Catalyst |  |  | According to the invention | StdT |  | StdT |
| Pressure | barg |  | 20 | 15 |  | 15 |
| Inlet temperature | ° C. |  | 50 | 40 |  | 45 |

TABLE 1-continued

|  |  | Starting material | 1st stage | 2nd stage | Raff2 | 3rd stage |
|---|---|---|---|---|---|---|
| Fresh feed throughput | kg/lh |  | 3 | 4.4 |  | 6 |
| (whsv) |  |  |  |  |  |  |
| Amount recirculated/ amount of fresh feed |  |  | 10 | 4 |  | 0 |
| Reaction conditions |  |  | adiabatic | adiabatic |  | Adiabatic |
| :Content of inerts in the hydrogen | % by volume |  | 10 | 10 |  | 0 |

Metathesis Procedure:

Olefin streams which have been prepared by the processes indicated in the description, for example a crude C4 fraction is treated by means of a selective hydrogenation according to the invention and isobutene present is then removed by etherification using methods known from the literature to a residual content of <3%, are used.

The C4-olefin stream having the composition indicated in each case is firstly passed over a 13× molecular sieve in order to remove oxygen-comprising compounds, compressed to the reaction pressure of 40 bar, mixed in the ratio indicated with freshly added ethene (measurement per difference weighing) and the appropriate C4 recycle stream is set. The C4 recycle stream is selected so that a total butene conversion of 60% is achieved. Amounts of C4 obtained above this are removed from the system so as not to allow accumulation of butanes (C4 purge). The C5 recycle stream separated off in the 3rd column is recirculated in its entirety to a point upstream of the reactor in order to suppress the cross-metathesis between 1-butene and 2-butene. The reaction mixture is subjected to metathesis in a 500 ml tube reactor by means of a 10% $Re_2O_7$ catalyst (on $Al_2O_3$) prepared as described in the literature. The reaction temperature is indicated in each case.

The output is separated by means of three columns into a C2/3 stream, a C4 stream, a C5 stream and a C6 stream and the individual streams are analyzed by gas chromatography.

The balances were in each case determined for a period of 24 hours at a constant reaction temperature.

Example 1

Comparative Example, not According to the Invention

Use of a Raffinate II Comprising 93 Ppm of 1,3-butadiene and 25 ppm of propadiene
Plant Settings:

| Space velocity over the catalyst (total flow through the reactor): | 5.0 kg/kg of cat/h |
|---|---|
| Raffinate II: | 870 g/h |
| C4 recycle: | 630 g/h |
| Ethene feed: | 65 g/h |

Composition of the Feed
1-Butene: 52.8%
2-Butene: 34.1%
n-Butane: 9.4%
i-Butane: 1.9%
i-Butene: 1.8%
(Balance comprises inert C3-, C4- and C5-hydrocarbons).
1

Figure 1:
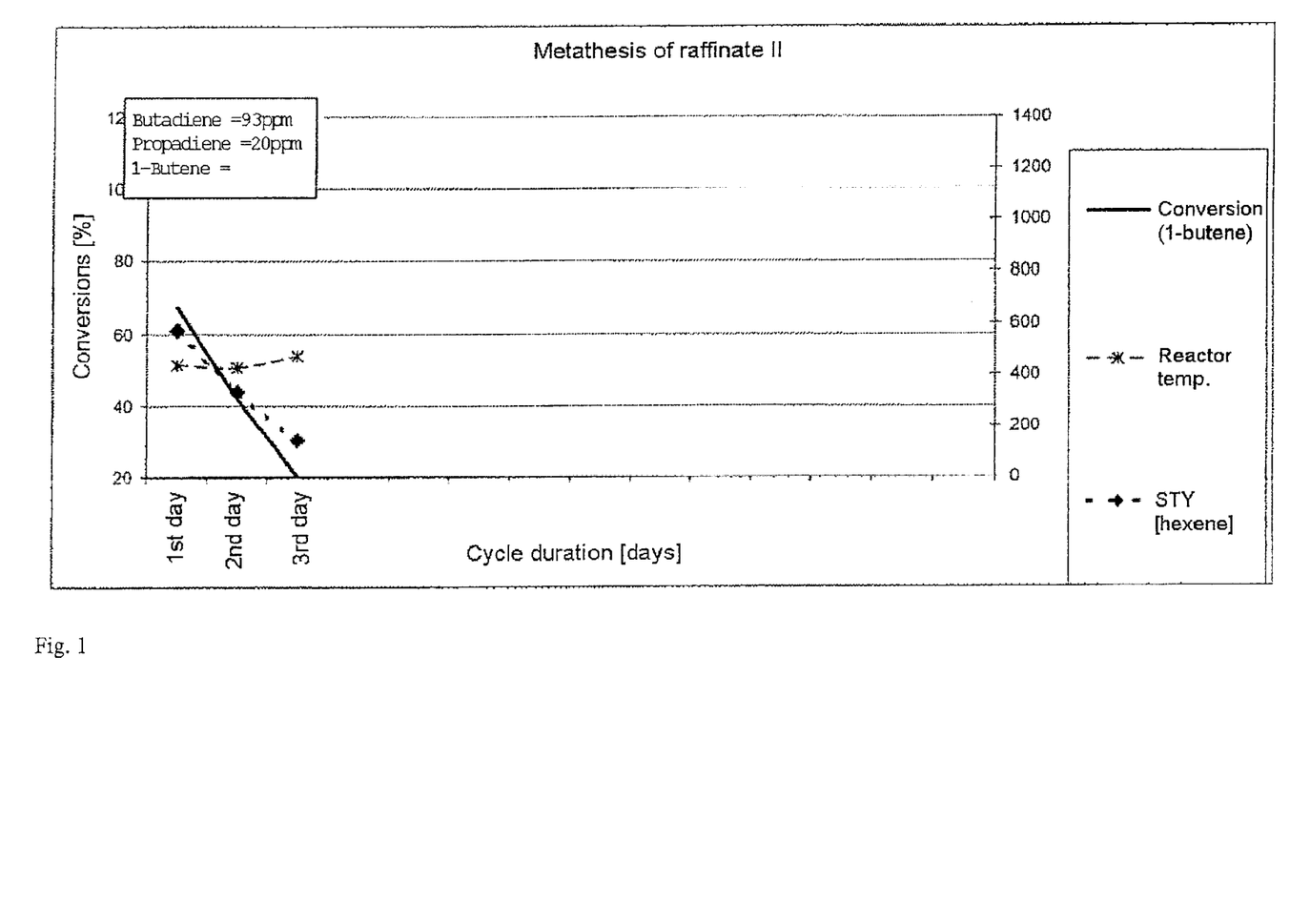
FIG. 1 depicts the presentation of the results in the metathesis reaction according to Example 1.

Presentation of the Results:

As depicted in FIG. 1, deactivation takes place, and the production of the desired products 3-hexene and propene drops to virtually zero after only three days.

Example 2

Comparative Example, not According to the Invention

Use of a Raffinate II Comprising 93 Ppm of 1,3-butadiene and 25 ppm of propadiene
Plant Settings:

| Space velocity over the catalyst (total flow through the reactor): | 3.0 kg/kg of cat/h |
|---|---|
| Raffinate II: | 500 g/h |
| C4 recycle: | 400 g/h |
| Ethene feed: | 40 g/h |

Figure 2:
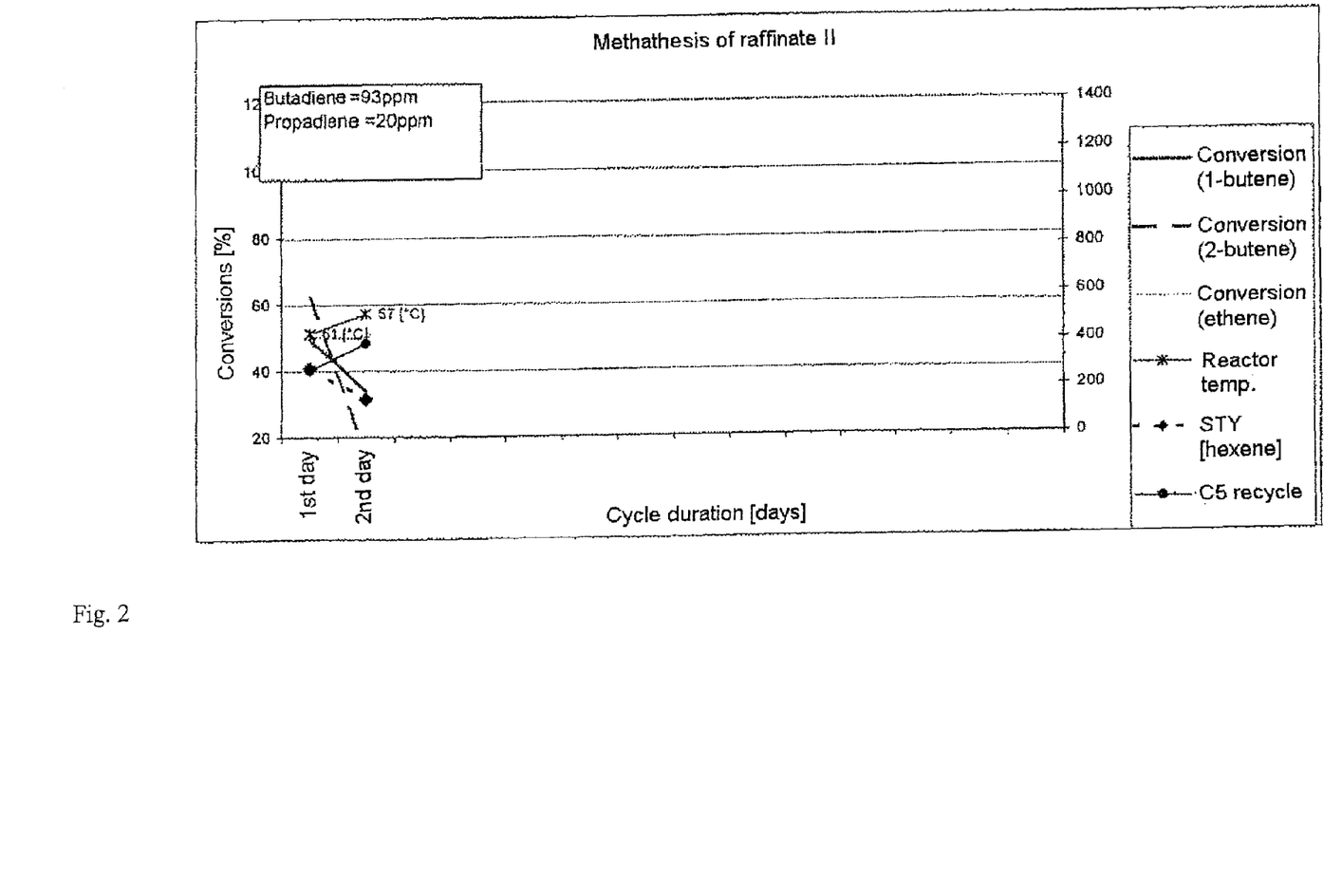
FIG. 2 depicts the presentation of the results in the metathesis reaction according to Example 2.

Composition of the Feed
1-Butene: 53.3%
2-Butene: 32.8%
n-Butane: 9.1%
i-Butane: 1.9%
i-Butene: 1.8%
(Balance comprises inert C3-, C4- and C5-hydrocarbons).
Presentation of the Results:

As depicted in FIG. 2, rapid deactivation takes place, and the production of the desired products 3-hexene and propene drops to virtually zero after only two days.

Example 3

According to the Invention

Use of a Raffinate II Comprising 150 ppm of 1,3-butadiene, 2 ppm of propadiene
Plant Settings:

| Space velocity over the catalyst: | 5 kg/kg of cat/h |
|---|---|
| Raffinate II: | 930 g/h |
| C4 recycle: | 560 g/h |
| Ethene feed: | 70 g/h |

Figure 3:
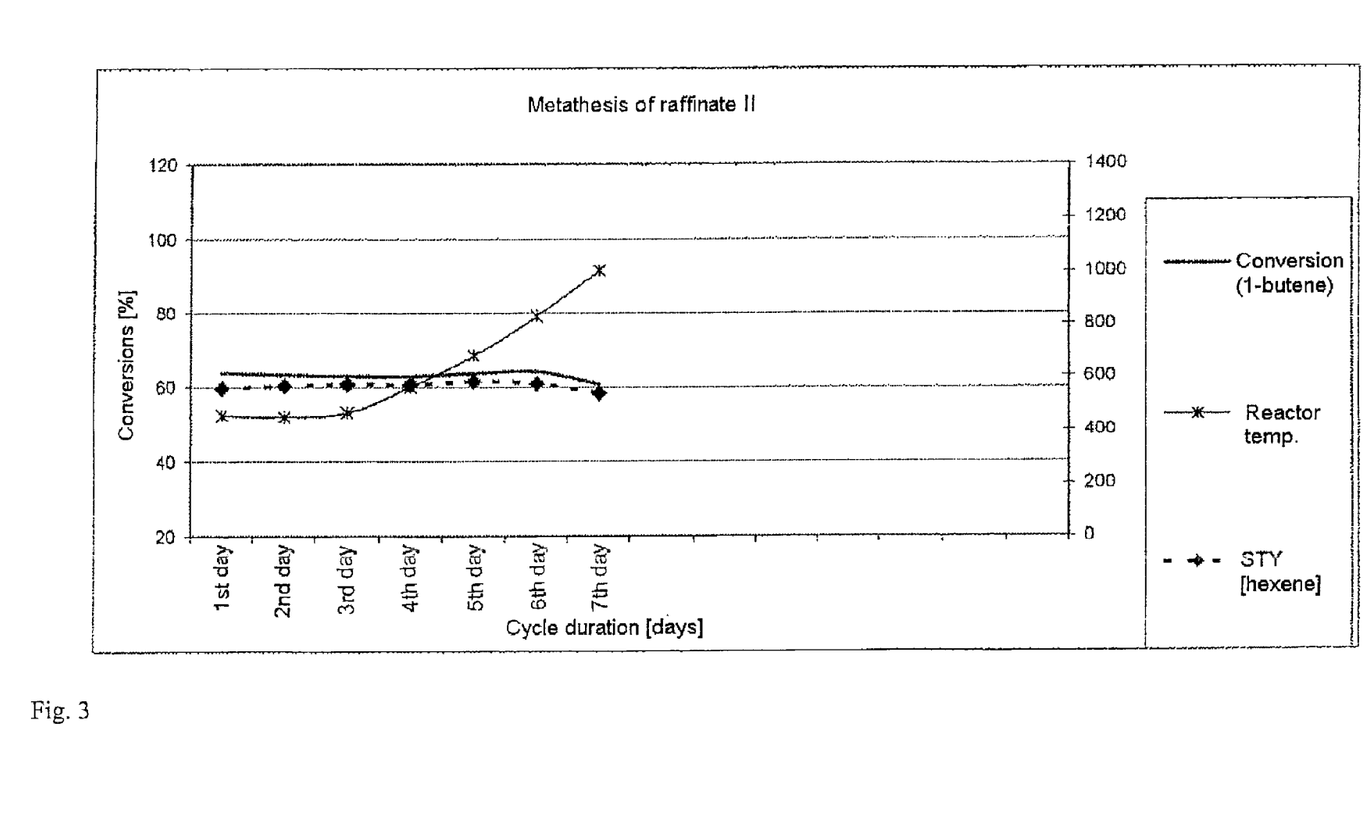
FIG. 3 depicts the presentation of the results in the metathesis reaction according to Example 3.

Composition of the Feed
1-Butene: 51.3%
2-Butene: 33.3%
n-Butane: 10.6%
i-Butane: 2.1%
i-Butene: 2.2%
(Balance comprises inert C3-, C4- and C5-hydrocarbons).
Presentation of the Results:

As depicted in FIG. 3, the activity of the catalyst can be kept constant by appropriately increasing the reaction temperature. The yield of desired products is thus considerably greater than in the cases 1+2.

Example 4

According to the Invention

Use of a Raffinate II Comprising 62 ppm of 1,3-butadiene, 2 ppm of propadiene and 8 ppm of 1,2-butadiene
Plant Settings:

| | |
|---|---|
| Space velocity over the catalyst: | 6 kg/(kg of cat/h) |
| Raffinate II: | 1120 g/h |
| C4 recycle: | 650 g/h |
| Ethene feed: | 98 g/h |

Figure 4:
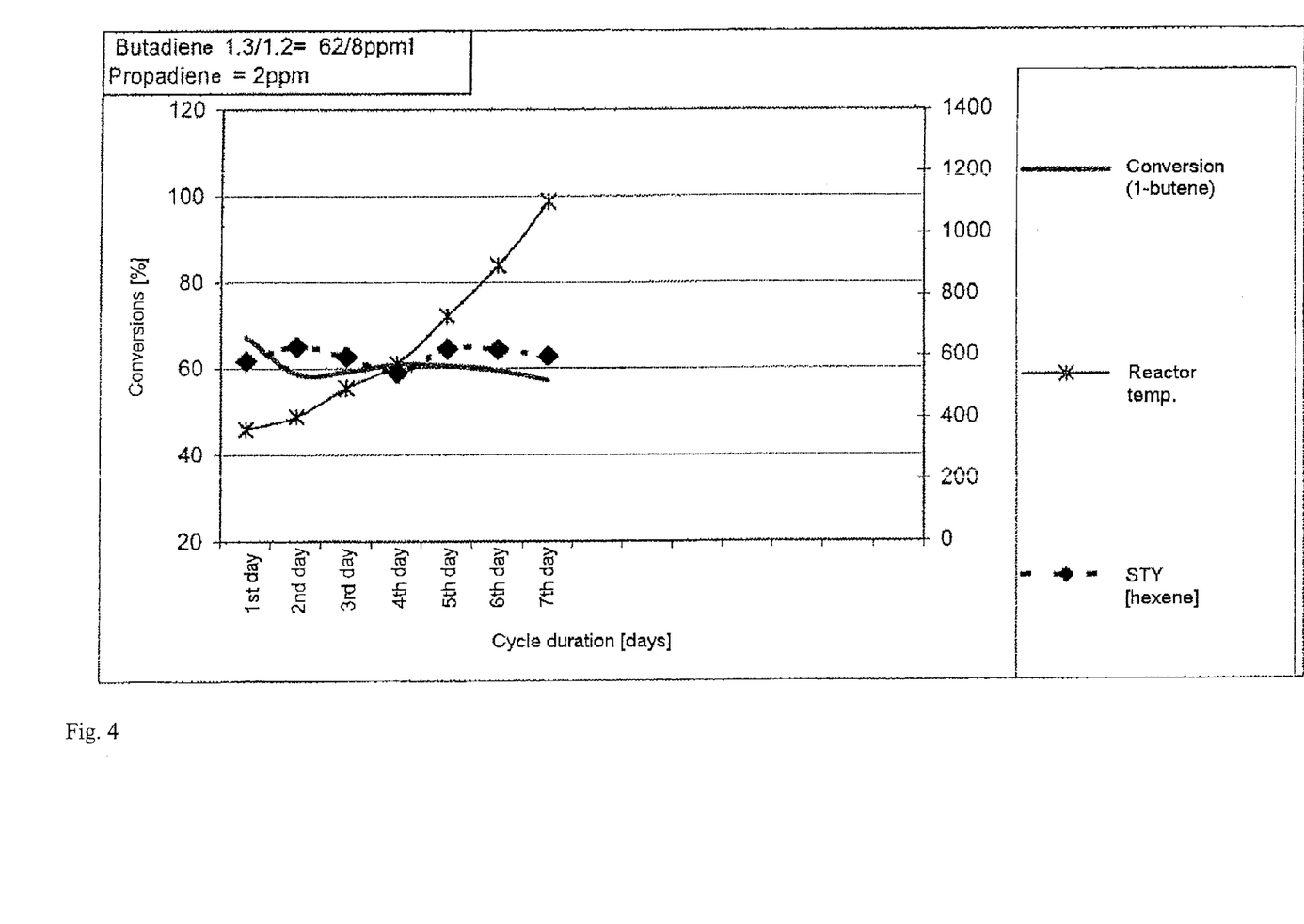
FIG. 4 depicts the presentation of the results in the metathesis reaction according to Example 4.

Composition of the Feed
1-Butene: 51.5%
2-Butene: 32.4%
n-Butane: 11.6%
i-Butane: 2.2%
i-Butene: 1.8%
(Balance comprises inert C3-, C4- and C5-hydrocarbons).
Presentation of the Results:

As depicted in FIG. 4, the activity of the catalyst can be kept constant by appropriately increasing the reaction temperature. The yield of desired products is thus considerably greater than in the cases 1+2.

The invention claimed is:

1. A C4-olefin mixture comprising a 1,3-butadiene content of from 100 to 500 ppm and a content in cumulated dienes of 1 to 10 ppm, wherein the 1-butene content in the mixture is at least 30% by weight, based on the mixture.

2. The C4-olefin mixture according to claim 1, wherein the content of cumulated 1,2-dienes is less than 10 ppm.

3. The C4-olefin mixture according to claim 1, wherein the ratio of 1-butene to 2-butenes in the mixture is from 1.2 to 2.0.

4. The C4-olefin mixture according to claim 1, wherein the mixture comprises 1-butene, trans-2-butene, cis-2-butene, isobutene, isobutane and n-butane.

* * * * *